United States Patent
Roh et al.

(10) Patent No.: US 9,607,106 B2
(45) Date of Patent: Mar. 28, 2017

(54) METHOD AND APPARATUS FOR SEARCHING PATTERN IN SEQUENCE DATA

(71) Applicant: Samsung Electronics Co., Ltd., Suwon-si (KR)

(72) Inventors: Yo-Han Roh, Hwaseong-si (KR); Hyoung-Min Park, Seoul (KR); Joo-Hyuk Jeon, Seoul (KR); Seok-Jin Hong, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 308 days.

(21) Appl. No.: 14/193,320

(22) Filed: Feb. 28, 2014

(65) Prior Publication Data

US 2014/0258327 A1    Sep. 11, 2014

(30) Foreign Application Priority Data

Feb. 28, 2013  (KR) ........................ 10-2013-0022421

(51) Int. Cl.
*G06F 17/30* (2006.01)
*G06K 9/62* (2006.01)
*G06F 19/24* (2011.01)

(52) U.S. Cl.
CPC ......... *G06F 17/30985* (2013.01); *G06K 9/62* (2013.01); *G06F 19/24* (2013.01)

(58) Field of Classification Search
CPC .......... G06F 17/30539; G06F 17/3053; G06F 11/1068; G06F 3/167; G06F 3/04892;
(Continued)

(56) References Cited

U.S. PATENT DOCUMENTS

| 6,125,206 A * | 9/2000 | Yokota | ............... G06K 9/6255 |
| | | | 382/189 |
| 2001/0007985 A1* | 7/2001 | Rothberg | ............... C12N 15/10 |
| | | | 707/E17.014 |

(Continued)

FOREIGN PATENT DOCUMENTS

| JP | 2010-44649 A | 2/2010 |
| JP | 2011-138422 A | 7/2011 |

(Continued)

OTHER PUBLICATIONS

T.K. Attwood—"The quest to deduce protein function from sequence: the role of pattern databases"—www.elsevier.com/locate/ijbcb—The International Journal of Biochemistry & Cell Biology—vol. 32, Issue 2, Feb. 2000, pp. 139-155.*

(Continued)

*Primary Examiner* — Anh Ly
(74) *Attorney, Agent, or Firm* — NSIP Law

(57) ABSTRACT

A method of searching a pattern in sequence data includes setting a plurality of interest pattern models each including an interest pattern length, an allowed mismatch value, and a minimum support; calculating a support of a candidate pattern that is generable within the interest pattern length based on the allowed mismatch value of at least one of the plurality of interest pattern models; and determining whether the support of the candidate pattern fulfills a condition of the minimum support of at least one of the plurality of interest pattern models.

29 Claims, 12 Drawing Sheets

(58) Field of Classification Search
CPC .. G06F 12/0292; G06F 12/0802; G06F 17/10; G06F 17/2765; G06F 17/30011; G06F 17/30256; G06F 17/30312; G06F 17/30336; G06F 17/30345; G06F 17/30368; G06F 17/30548; G06F 19/24; G06F 19/3443; G06F 17/30985; G06K 9/62

See application file for complete search history.

(56) References Cited

U.S. PATENT DOCUMENTS

| | | | | |
|---|---|---|---|---|
| 2003/0220771 A1* | 11/2003 | Vaidyanathan | ......... | G06F 19/22 703/2 |
| 2005/0022115 A1* | 1/2005 | Baumgartner | .... | G06F 17/30911 715/205 |
| 2007/0073372 A1* | 3/2007 | Heath | ...................... | A61N 1/20 607/145 |
| 2007/0219992 A1* | 9/2007 | Bollinger | .......... | G06F 17/30539 707/E17.014 |
| 2007/0220030 A1* | 9/2007 | Bollinger | .......... | G06F 17/30539 707/E17.108 |
| 2009/0049551 A1* | 2/2009 | Ahn | ...................... | G06F 21/562 726/23 |
| 2009/0076817 A1* | 3/2009 | Jeon | ...................... | G10L 15/187 704/240 |
| 2009/0254971 A1* | 10/2009 | Herz | ...................... | G06Q 10/10 705/1.1 |
| 2010/0063774 A1* | 3/2010 | Cook | ...................... | G05B 15/02 702/181 |
| 2012/0165638 A1* | 6/2012 | Duke | ................. | A61B 5/14532 600/365 |
| 2012/0226492 A1* | 9/2012 | Tsuboi | ............. | G06F 17/30684 704/9 |
| 2013/0338453 A1* | 12/2013 | Duke | ................... | A61B 5/7282 600/309 |

FOREIGN PATENT DOCUMENTS

| KR | 10-2010-0137963 A | 12/2010 |
|---|---|---|
| KR | 10-1079063 B1 | 11/2011 |

OTHER PUBLICATIONS

Haixun Wang Chang-Shing Perng Wei Fan Philip S. Yu—An Index Structure for Pattern Similarity Searching in DN A Microarray Data—Proceedings of the IEEE Computer Society Bioinformatics Conference (CSB'02)—pp. 1-12.*

A. Floratou, et al., "Efficient and Accurate Discovery of Patterns in Sequence Datasets," *IEEE Transactions on Knowledge and Data Engineering*, vol. 23, No. 8, Aug. 2011, pp. 1154-1168, originally published Apr. 5, 2011, revised Jun. 20, 2011.

Floratou, Avrilia, et al. "Efficient and Accurate Discovery of Patterns in Sequence Data Sets," *Knowledge and Data Engineering, IEEE Transactions on* 23.8 (2011): 1154-1168. (16 pages, in English).

Extended European Search Report issued on Jan. 5, 2016 in counterpart European Patent Application No. 14157216 (9 pages, in English).

* cited by examiner

CANDIDATE PATTERN: aa

| SIMILAR PATTERN | SUPPORT | MISMATCH VALUE |
|---|---|---|
| aa | 2 | 0 |
| ab | 2 | 1 |
| ba | 2 | 1 |
| bb |  | 2 > D |

CANDIDATE PATTERN: aaa

| SIMILAR PATTERN | SUPPORT | MISMATCH VALUE |
|---|---|---|
| aaa | 0 | 0 |
| aab | 2 | 1 |
| aba | 1 | 1 |
| abb |  | 2 > D |
| baa | 1 | 1 |
| bab |  | 2 > D |
| bba |  | 2 > D |
| bbb |  | 3 > D |

CANDIDATE PATTERN: aa

| SIMILAR PATTERN | SUPPORT | MISMATCH VALUE |
|---|---|---|
| aa | 2 | 0 |
| ab | 2 | 1 |
| ba | 2 | 1 |
| bb | 1 | 2 |

CANDIDATE PATTERN: aaa

| SIMILAR PATTERN | SUPPORT | MISMATCH VALUE |
|---|---|---|
| aaa | 0 | 0 |
| aab | 2 | 1 |
| aba | 1 | 1 |
| abb | 1 | 2 |
| baa | 1 | 1 |
| bab | 1 | 2 |
| bba | 1 | 2 |
| bbb |  | 3 > D |

METHOD AND APPARATUS FOR SEARCHING PATTERN IN SEQUENCE DATA

CROSS-REFERENCE TO RELATED APPLICATIONS

This application claims the benefit under 35 USC 119(a) of Korean Patent Application No. 10-2013-0022421 filed on Feb. 28, 2013, in the Korean Intellectual Property Office, the entire disclosure of which is incorporated herein by reference for all purposes.

BACKGROUND

1. Field

The following description relates to a method and an apparatus for searching a pattern in sequence data.

2. Description of Related Art

Pattern searching defines an interest pattern form, and extracts a specific pattern frequently generated from sequence data. The searched interest pattern may be used in various data mining technologies, such as data classification and clustering, etc., and may also be used in various application fields, such as bio, medical, and IT industries, etc.

In addition, in pattern searching, an interest pattern model defining a pattern form may be used. That is, a pattern that fulfills the conditions of the interest pattern model can be searched using an interest pattern length, an allowed mismatch value, and a minimum support included in the interest pattern model.

However, as a sequence data size continuously increases due to rapid development of sensor devices and data acquisition technologies, searching for a support of candidate patterns requires a large amount of computation. If the interest pattern model has various allowed mismatch values, or various minimum supports, the number of support searches sharply increases, so an effective searching method is needed.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method of searching a pattern in sequence data includes setting a plurality of interest pattern models each including an interest pattern length, an allowed mismatch value, and a minimum support; calculating a support of a candidate pattern that is generable within the interest pattern length of at least one of the plurality of interest pattern models based on the allowed mismatch value of at least one of the plurality of interest pattern models; and determining whether the support of the candidate pattern fulfills a condition of the minimum support of at least one of the plurality of interest pattern models.

The calculating of the support of the candidate pattern may include calculating the support of a candidate pattern that is generable within a maximum interest pattern length of the plurality of the interest pattern models.

The calculating of the support of the candidate pattern may include, in a case where the allowed mismatch value is the same in each of the plurality of interest pattern models, generating a set of similar patterns having a mismatch value compared to the candidate pattern within a range of the allowed mismatch value; and calculating a support of each of the similar patterns in the set.

The determining of whether the support of the candidate pattern fulfills the condition of the minimum support of at least one of the plurality of interest pattern models may include determining whether a support sum of the similar patterns in the set fulfills a condition of the minimum support of each of the plurality of interest pattern models.

The calculating of the support of the candidate pattern may include, in a case where the allowed mismatch value is different in at least two of the plurality of interest pattern models, generating a set of similar patterns having a mismatch value compared to the candidate pattern within a range of a maximum allowed mismatch value of the plurality of interest pattern models; and calculating a support of each of the similar patterns in the set.

The determining of whether the support of the candidate pattern fulfills the condition of the minimum support of at least one of the plurality of interest pattern models may include determining, for each of the plurality of interest pattern models, whether a support sum of similar patterns in the set fulfilling a condition of the allowed mismatch value of the interest pattern model fulfills the condition of the minimum support of the interest pattern model.

In another general aspect, a method of searching a pattern in sequence data includes setting a plurality of interest pattern models each including an interest pattern length, an allowed mismatch value, and a minimum support; determining whether a support of a parent pattern is greater than or equal to the minimum support of the plurality of interest pattern models; in a case where the support of the parent pattern is greater than or equal to the minimum support of at least one interest pattern model of the plurality of interest pattern models, calculating a support of a child pattern based on the allowed mismatch value of the at least one interest pattern model; and determining whether the support of the child pattern fulfills a condition of the minimum support of the at least one interest pattern model.

The calculating of the support of the child pattern may include, in a case where a parent pattern length is less than a maximum interest pattern length of the at least one interest pattern model, calculating the support of the child pattern.

The calculating of the support of the child pattern may include, in a case where the allowed mismatch value is the same in each of the at least one interest pattern model, generating a set of similar patterns within a range of the allowed mismatch value of the at least one interest pattern model; and calculating a support of each of the similar patterns in the set.

The determining of whether the support of the child pattern fulfills the condition of the minimum support of the at least one interest pattern model may include determining whether a support sum of the similar patterns in the set fulfills a condition of the minimum support of each of the at least one interest pattern model.

The calculating of the support of the child pattern may include generating a set of similar patterns within a range of a maximum allowed mismatch value of the at least one interest pattern model; and calculating a support of each of the similar patterns in the set.

The determining of whether the support of the child pattern fulfills the condition of the one minimum support of the at least one interest pattern model may include determining, for each of the at least one interest pattern model, whether a support sum of similar patterns in the set fulfilling a condition of the allowed mismatch value of the interest pattern model fulfills a condition of the minimum support of the interest pattern model.

In another general aspect, a method of searching a pattern in sequence data includes setting an interest pattern model including an interest pattern length, an allowed mismatch value, and a minimum support; determining whether a support of a parent pattern is greater than or equal to the minimum support; and in a case where the support of the parent pattern is greater than or equal to the minimum support, calculating a support of a child pattern that is generable from the parent pattern using mismatch values of similar patterns of the parent pattern.

The calculating of the support of the child pattern may include generating a first set of patterns by appending a unit pattern to similar patterns of the parent pattern having a mismatch value less than the allowed mismatch value; generating a second set of patterns by appending a unit pattern to similar patterns of the parent pattern having a mismatch value equal to the allowed mismatch value; calculating a support of each of the patterns in the first set and the second set; and calculating the support of the child pattern using the support of each of the patterns in the first set and the second set.

The calculating of the support of the child pattern may further include generating the child pattern by appending a unit pattern to the parent pattern; adding a sum support of the patterns in the first set and a support of a pattern in the second set derived by appending a same unit pattern appended to the parent pattern to generate the child pattern; and determining whether a result of the adding fulfills a condition of the minimum support.

The method may further include, in a case where at least one child pattern derived from the parent pattern fulfills a condition of the minimum support and has a length less than the interest pattern length, calculating a mismatch value by comparing each of the at least one child fulfilling the condition of the minimum support with each of the patterns in the first set and the second set.

In another general aspect, a method of searching a pattern in sequence data includes setting an interest pattern model including an interest pattern length, an allowed mismatch value, and a minimum support; determining whether a support of a parent pattern is greater than or equal to the minimum support; and in a case where the support of the parent pattern is greater than or equal to the minimum support, calculating a support of a child pattern that is generable from the parent pattern using mismatch values and supports of similar patterns of the parent pattern.

The calculating of the support of the child pattern may include generating a set of patterns by appending a unit pattern to similar patterns of the parent pattern having a mismatch value equal to the allowed mismatch value; calculating a support of each of the patterns in the set; and calculating the support of the child pattern using the support of the patterns in the set and a support of similar patterns of the parent pattern having a mismatch value less than the allowed mismatch value.

The calculating of the support of the child pattern may further include generating the child pattern by appending a unit pattern to the parent pattern; and calculating the support of the child pattern by adding the support of each of the patterns in the set derived by appending a same unit pattern appended to the parent pattern to generate the child pattern, and the support of each of the similar patterns having the mismatch value less than the allowed mismatch value.

The method may further include, in a case where at least one child pattern that is generable from the parent application fulfills a condition of the minimum support and has a length less than the interest pattern length, generating a set of patterns by appending a unit pattern to similar patterns of the parent pattern having a mismatch value less than the allowed mismatch value; and calculating a support of each of the patterns in the set.

In another general aspect, an apparatus for searching a pattern in sequence data includes an interest pattern model setter configured to set a plurality of interest pattern models each including an interest pattern length, an allowed mismatch value, and a minimum support; a support calculator configured to calculate a support of a candidate pattern generable within the interest pattern length of at least one of the plurality of interest pattern models based on the allowed mismatch value of at least one of the plurality of interest pattern models; and a determiner configured to determine whether the support of the candidate pattern fulfills a condition of the minimum support of at least one of the plurality of interest pattern models.

In a case where the allowed mismatch value is the same in each of the plurality of interest pattern models, the support calculator may be further configured to generate a set of similar patterns having a mismatch value compared to the candidate pattern within a range of the allowed mismatch value; and calculate a support of each of the similar patterns in the set.

The determiner may be further configured to determine whether a support sum of the similar patterns in the set fulfills a condition of the minimum support of each of the plurality of interest pattern models.

In a case where the allowed mismatch value is different in at least two of the plurality of interest pattern models, the support calculator may be further configured to generate a set of similar patterns having a mismatch value compared to the candidate pattern within a range of a maximum allowed mismatch value of the plurality of interest pattern models; and calculate a support of each of the similar patterns in the set.

The determiner may be further configured to determine, for each of the plurality of interest pattern models, whether a support sum of similar patterns in the set fulfilling a condition of the allowed mismatch value of the interest pattern model fulfills the condition of the minimum support of the interest pattern model.

In a case where the support of the candidate pattern fulfills the condition of the minimum support of the at least one of the plurality of interest pattern models and the candidate pattern has a length less than a maximum interest pattern length of the at least one of the plurality of interest pattern models, the support calculator may be further configured to calculate a support of a child pattern that is generable from the candidate pattern using a mismatch value of each pattern of similar patterns of the candidate pattern; and the determiner may be further configured to determine whether the child pattern fulfills conditions of the at least one of the plurality of interest pattern models of which the condition of the minimum support is fulfilled by the candidate pattern.

In another general aspect, a method of searching a pattern in sequence data includes setting a plurality of interest pattern models each including an interest pattern length, an allowed mismatch value, and a minimum support, wherein the allowed mismatch value is different in each of the plurality of interest pattern models; generating all possible similar patterns of a candidate pattern within the interest pattern length; calculating a support and a mismatch value of each of the similar patterns; determining, for each of the plurality of interest pattern models, whether the candidate pattern fulfills conditions of the interest pattern model based on the support of only those similar patterns having a mismatch value less than or equal to the mismatch value of the interest pattern model.

The determining may include calculating a support sum of only those similar patterns having a mismatch value less than or equal to the mismatch value of the interest pattern model; comparing the support sum with the minimum support of the interest pattern model; in a case where the support sum is greater than or equal to the minimum support of the interest pattern model, determining that the candidate pattern fulfills the conditions of the interest pattern model; and in a case where the support sum is less than the minimum support of the interest pattern model, determining that the candidate pattern does not fulfill the conditions of the interest pattern model.

The minimum support may be different in each of the plurality of interest pattern models.

Other features and aspects will be apparent from the following detailed description, the drawings, and the claims.

BRIEF DESCRIPTION OF THE DRAWINGS

FIGS. 5A and 5B are diagrams illustrating examples of a method of searching a pattern in a case where a plurality of interest pattern models each have the same allowed mismatch value.

FIGS. 6A and 6B are diagrams illustrating examples of a method of searching a pattern in a case where a plurality of interest pattern models each have different allowed mismatch values.

DETAILED DESCRIPTION

Figure 1:
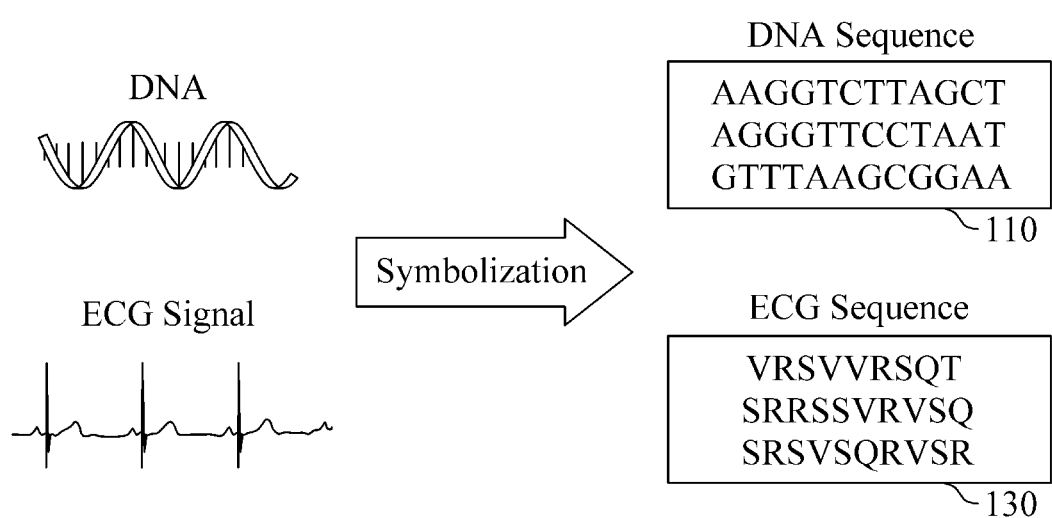
FIG. 1 is a diagram illustrating an example of sequence data.

The following description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 is a diagram illustrating an example of sequence data.

Referring to FIG. 1, sequence data is data that is arranged based on predetermined rules with respect to successive events. The sequence data may be data successively arranged, such as a DNA sequence 110 composed of bases A, G, C, and T as illustrated in FIG. 1, or an electrocardiogram (ECG) sequence 130, which shows data measured from an electrocardiogram with specific expressible symbols as illustrated in FIG. 1. However, the sequence data is not limited to the examples illustrated here, which may be shown in various forms, such as specific words, characters, or numbers.

A unit pattern is the shortest unit included in the sequence data. For example, the unit patterns of the DNA sequence data 110 are A, G, T, and C, and the unit patterns of the ECG sequence 130 are Q, R, S, T, V. A pattern is a combination of successive unit patterns. A pattern length is the number of unit patterns that are included in the pattern. Hereafter, the terms 'sequence data', 'pattern', 'pattern length', and 'unit pattern' will have the meanings defined above.

Figure 2:
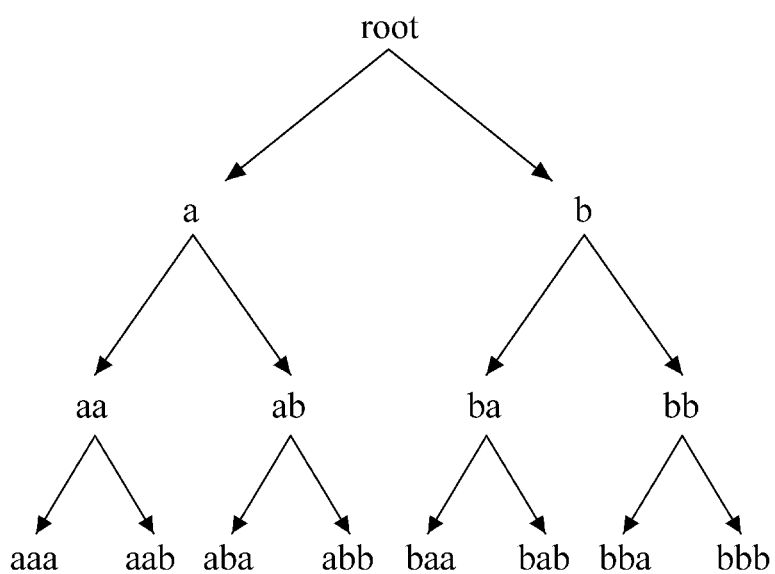
FIG. 2 is a diagram illustrating an example of candidate patterns.

FIG. 2 is a diagram illustrating an example of candidate patterns.

In the example in FIG. 2, sequence data is composed of unit patterns 'a' and 'b'. For an interest pattern model whose length is 3, all of the generable candidate patterns are shown in FIG. 2. In other words, each candidate pattern has a length less than or equal to 3, and may be generated as any one of the available unit patterns 'a' and 'b' or any combination of the available unit patterns 'a' and 'b'.

Whether the candidate pattern fulfills the conditions of the interest pattern model may be determined sequentially from the shortest parent pattern 'a' or 'b' to child patterns. A child pattern is a pattern generated by appending a unit pattern to a parent pattern. For example, as illustrated in FIG. 2, child patterns of 'a' are 'aa' and 'ab', and child patterns of 'aa' are 'aaa' and 'aab'. Conversely, 'a' is the parent pattern of 'aa' and 'ab', and 'aa' is the parent pattern of 'aaa' and 'aab'. In addition, 'aaa' and 'aab' are the child patterns of 'aa', and are also grandchild patterns of 'a'. Hereafter, the terms 'parent pattern', 'child pattern', and 'grandchild pattern' will have the meanings defined above.

Figure 3:
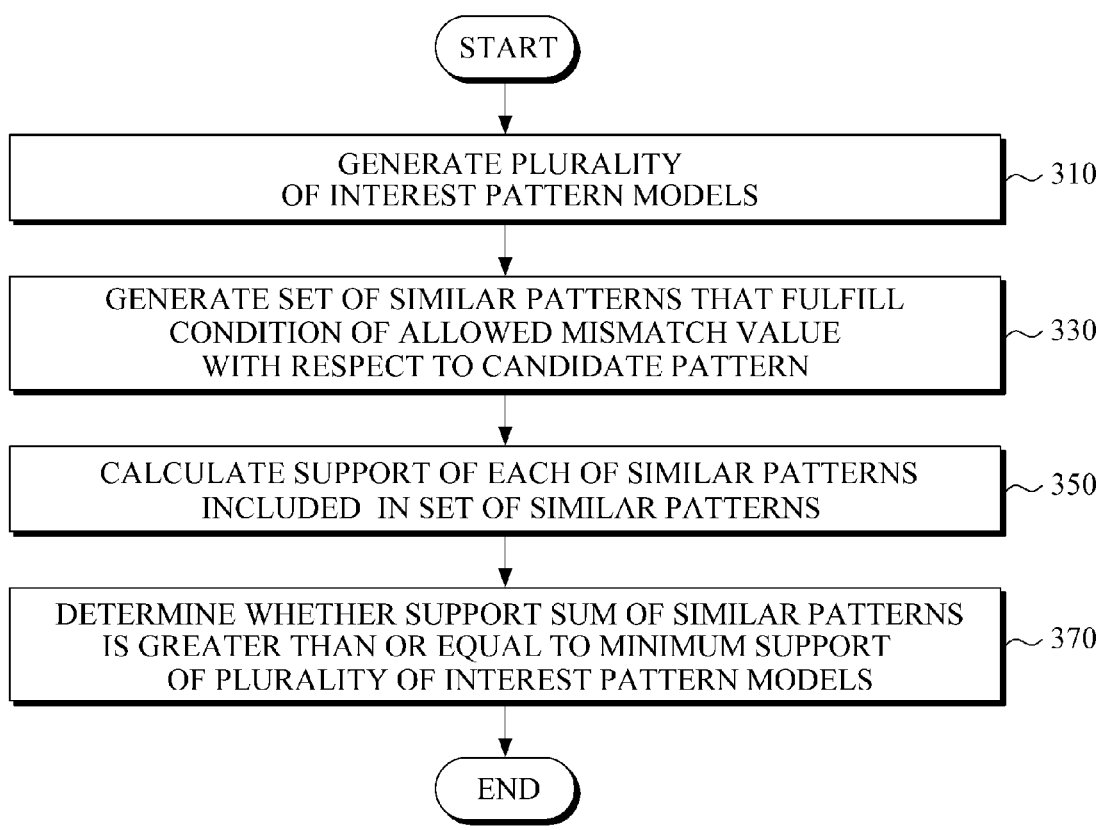
FIG. 3 is a flowchart illustrating an example of a method of searching a pattern in sequence data.

FIG. 3 is a flowchart illustrating an example of a method of searching a pattern in sequence data.

A plurality of interest pattern models each including an interest pattern length, an allowed mismatch value, and a minimum support are generated in 310.

An interest pattern is a pattern whose support is greater than or equal to a minimum support within a range of the allowed mismatch value of the interest pattern model, and whose length fulfills a condition of the interest pattern length.

The support indicates how many times a specific pattern appears in sequence data, and the minimum support indicates the lowest support required for the specific pattern to be included in the interest patterns. In obtaining a support of a specific pattern in the sequence data, the mismatch value is used to show the variance between patterns, and overcome noise that may be generated in the process of acquiring the sequence data. For example, a pattern 'ABAAAC' has the mismatch value of 1 compared to a pattern 'AAAAAC', and a pattern 'ABBAAC' has a mismatch value of 2 compared to the pattern 'AAAAAC'.

The interest pattern model may be set by a user. For example, in the case where the exact forms of meaningful patterns in the sequence data are known in advance, the user may set an interest pattern model by setting the interest pattern length, the allowed mismatch value, and the minimum support.

In the case where only approximate forms of the meaningful patterns are known, the user may set a plurality of interest pattern models each including the interest pattern length, the allowed mismatch value, and the minimum support of which at least one is different in each of the plurality of interest models.

In a case where the plurality of interest pattern models are generated in 310, a set of similar patterns of a predetermined candidate pattern within a range of the allowed mismatch value are generated in 330, and the support of each of the similar patterns included in the set is calculated in 350. For example, if the allowed mismatch value of all of the plurality of interest pattern models is 2, the support of the candidate pattern may be calculated by adding the support of each of the similar patterns whose mismatch value is 2 or less compared to the candidate pattern.

For another example, if the allowed mismatch values of two interest pattern models are 2 and 3, respectively, in the case of the allowed mismatch value 2, a support sum of similar patterns whose mismatch value is 2 or less when compared to the candidate pattern becomes a support of the candidate pattern. Also, in the case of the allowed mismatch value 3, a support sum of similar patterns whose mismatch value is 3 or less when compared to the candidate pattern becomes a support of the candidate pattern.

A support of each similar pattern can be figured out by a data structure that is used for searching the support, which has already been acquired in advance from the sequence data. The data structure for searching the support may be generated in advance and stored in a storage medium, such as a memory or a disk if the sequence data is input.

In addition, the data structure used for searching the support may use a suffix tree. For example, if the sequence data is composed of a combination of the unit patterns 'a' and 'b', the suffix tree may provide information about the support of all available patterns starting with the unit pattern 'a' or 'b'.

That is, if the suffix tree for searching the support in the sequence data has been generated and stored in advance in the storage medium, a support of specific patterns may be immediately obtained using path information in a suffix tree However, the data structure used for searching the support is not limited to the suffix tree. Various other types of data structures may be used, such as a hash table or any other type of data structure known to one of ordinary skill in the art.

After the support of the candidate pattern is obtained, whether the support of the candidate pattern is greater than or equal to the minimum support of the interest pattern model is determined in 370. More specifically, if the support of the candidate pattern obtained within a range of the allowed mismatch value of the interest pattern model is greater than or equal to the minimum support, and fulfills a condition of the interest pattern length, the candidate pattern is set as an interest pattern that fulfills the conditions of the interest pattern model.

Meanwhile, if the plurality of interest pattern models have the same allowed mismatch value, but have a different minimum support, it may be determined whether the support of the candidate pattern is greater than or equal to the minimum support of each interest pattern model. That is, supports of similar patterns included in a set of similar patterns that fulfill a condition of the allowed mismatch value are obtained without repeating generating similar pattern patterns and calculating a support for each interest pattern model. By these operations, it may be determined whether a condition of the minimum support is fulfilled with respect to all interest pattern models. Thus, the process of generating a similar pattern set and calculating the support of each of the similar patterns requiring a high calculation cost may be reduced.

Figure 4:
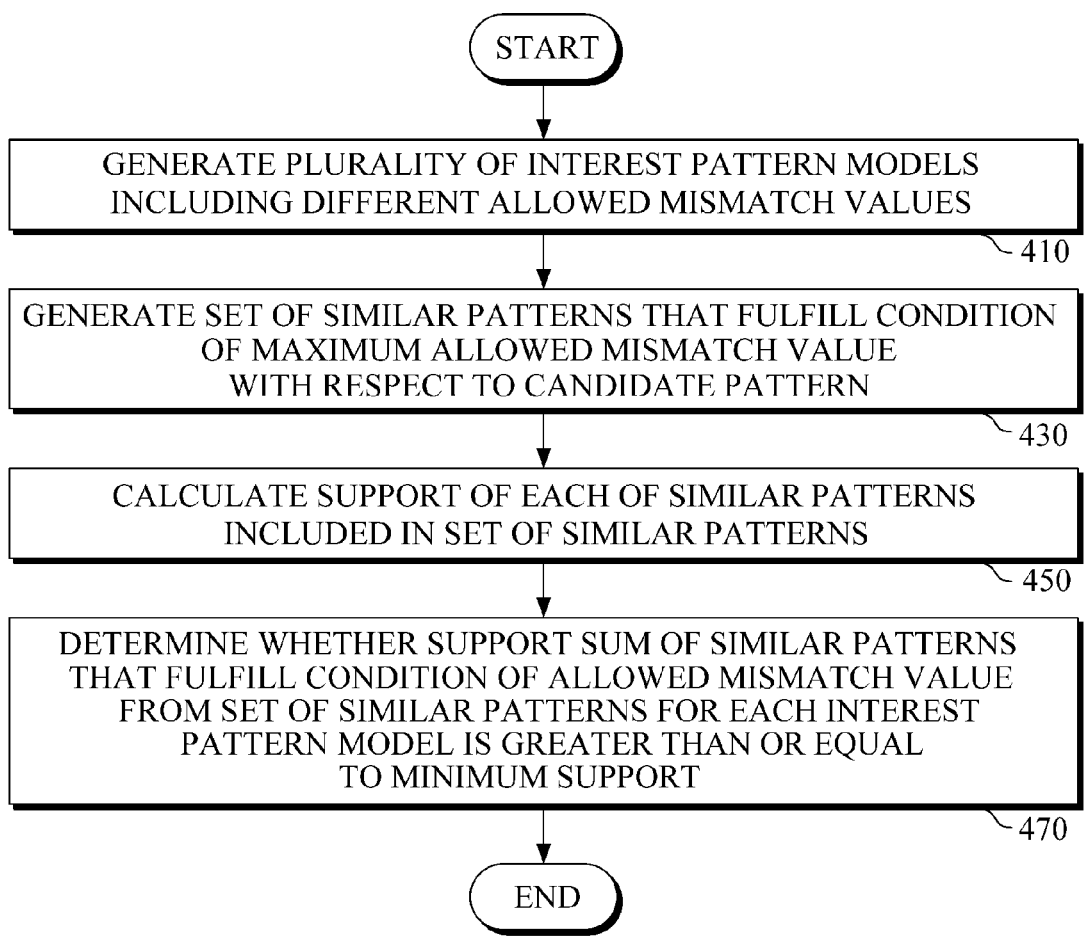
FIG. 4 is a flowchart illustrating an example of a method of searching a pattern in a case where one or more allowed mismatch values of a plurality of interest pattern models are different from the other allowed mismatch values.

FIG. 4 is a flowchart illustrating an example of a method of searching a pattern in a case where one or more allowed mismatch values of a plurality of interest pattern models are different from the other allowed mismatch values.

Referring to FIG. 4, if a plurality of interest patterns including different allowed mismatch values are generated in 410, a set of similar patterns of the candidate pattern that fulfill a condition of a maximum allowed mismatch value of the plurality of interest pattern models are generated in 430. The set of similar patterns of the candidate pattern fulfilling the condition of the maximum allowed mismatch value may include all similar patterns whose allowed mismatch values are less than or equal to the maximum allowed mismatch value.

Afterwards, a support of each of the similar patterns included in the set of similar patterns are calculated in 450. The support of each of the similar patterns may be obtained using a data structure used for searching a support that has been generated in advance.

Also, in a case where the support of each of the similar patterns included in the set of similar patterns is calculated, the support sum of the similar patterns that fulfill a condition of the allowed mismatch value for each interest pattern model is calculated from the set of similar patterns. Then, it is determined whether the support sum of the similar patterns is greater than or equal to the minimum support in 470. That is, the support of each of the similar patterns included in the set of similar patterns fulfilling a condition of the maximum allowed mismatch value is calculated without repeating generating a set of similar patterns and calculating a support for each interest pattern model. By these operations, it is determined whether a condition of the minimum support is fulfilled may be determined with respect to all the interest pattern models. Thus, the process of generating a set of similar patterns and calculating the support of each of the similar patterns requiring a high calculation cost may be reduced.

FIGS. 5A and 5B are diagrams illustrating examples of a method of searching a pattern in a case where a plurality of interest pattern models each have the same allowed mismatch value.

In FIGS. 5A and 5B, interest pattern models are P1=(L: 2-3, D: 1, K: 5) and P2=(L: 2-3, D: 1, K: 7), and 'a' and 'b' are available unit patterns. L represents an interest pattern length, D represents an allowed mismatch value, and K represents a minimum support.

Referring to FIG. 5A, the mismatch value 1 of each of similar patterns 'aa', 'ab', and 'ba' compared to a candidate pattern 'aa' is less than or equal to the allowed mismatch value 1 of each of P1 and P2. The support of each of 'aa', 'ab', and 'ba' in a data sequence (not shown) is 2. The support of the similar patterns in FIG. 5A and the similar patterns in FIGS. 5B, 6A, 6B, and 8 described below may be calculated from a data sequence using any of the techniques described above with respect to FIG. 3. However, the mismatch value 2 of the similar pattern 'bb' compared to the candidate pattern 'aa' is greater than the allowed mismatch value 1 of each of P1 and P2. As a result, the similar pattern 'bb' is not included in a set of similar patterns.

Also, by calculating the support for each of the similar patterns 'aa', 'ab', and 'ba', whether the candidate pattern 'aa' fulfills a condition of the minimum support of each of P1 and P2 may be determined.

That is, a support sum of the similar patterns 'aa', 'ab', and 'ba' is 6, so the candidate pattern 'aa' fulfills a condition of the minimum support 5 of P1. However, the support sum 6 does not fulfill a condition of the minimum support 7 of P2. In addition, the length of the candidate pattern 'aa' is 2, so the candidate pattern 'aa' is included in interest patterns that fulfill the conditions of the interest pattern model P1.

Referring to FIG. 5B, for a child candidate pattern 'aaa' of the candidate pattern 'aa', it need not be determined whether the child candidate pattern 'aaa' fulfills the conditions of P2. In other words, the child pattern 'aaa' is derived from the parent pattern 'aa' to which the unit pattern 'a' is added, so the support of the child pattern cannot be greater than the support of the parent pattern. Thus, in a case where the parent pattern does not fulfill the minimum support condition of the interest pattern model, the child pattern also does not fulfill the minimum support condition of the interest pattern model. Accordingly, as illustrated in FIG. 5B, where 'aaa' is the child pattern of 'aa', whether similar patterns of 'aaa' fulfill the minimum support condition of P2 not need to be determined.

Meanwhile, a set of similar patterns that fulfill a condition of an allowed mismatch value 1 of P1 with respect to the child pattern 'aaa' includes 'aaa', 'aab', 'aba', and 'baa'. Also, a support sum of 'aaa', 'aab', 'aba', and 'baa' included in the set of similar patterns is 4, so the child pattern 'aaa' does not fulfill the minimum support condition of 5 of P1. In addition, 'abb', 'bab', 'bba', and 'bbb' do not fulfill the allowed mismatch value condition of 1 of P1. As a result, 'abb', 'bab', 'bba', and 'bbb' are not included in the set of similar patterns.

FIGS. 6A and 6B are diagrams illustrating examples of a method of searching a pattern in a case where a plurality of interest pattern models each have different allowed mismatch values.

As illustrated in FIGS. 6A and 6B, interest pattern models are P1=(L: 2-3, D: 1, K: 5) and P2=(L2: 2-3, D: 2, K: 5), and 'a' and 'b' are available unit patterns.

Referring to FIG. 6A, a set of similar patterns includes 'aa', 'ab', 'ba', and 'bb' whose mismatch value compared to the candidate pattern 'aa' is less than or equal to the maximum allowed mismatch value 2 of respective allowed mismatch values 1 and 2 of P1 and P2. The set of similar patterns includes 'aa', 'ab', and 'ba' whose mismatch values are less than or equal to the allowed mismatch value 1 of P1.

In one example, in a case where a set of similar patterns is generated, whether the candidate pattern fulfills a condition of the minimum support of each of P1 and P2 may be determined by calculating a support of each similar pattern included in the set, and using both the support of each similar pattern and the mismatch value between each similar pattern and the candidate pattern.

In the example of FIG. 6A, an allowed mismatch value of P2 is 2. Also, a support sum of the similar patterns 'aa', 'ab', 'ba', and 'bb', whose mismatch values compared to the candidate pattern 'aa' are less than or equal to the allowed mismatch value of 2 of P2, is 7. So the candidate pattern 'aa' fulfills a condition of the minimum support of P2. Likewise, the allowed mismatch value of P1 is 1. Also, a support sum of the similar patterns 'aa', 'ab', and 'ba', whose mismatch values compared to the candidate pattern 'aa' are less than or equal to the allowed mismatch value of 1 of P1, is 6. Thus, the candidate pattern 'aa' fulfills a condition of the minimum support of P1 as well.

In other words, in a case where a plurality of interest pattern models have a different allowed mismatch value as in the example of FIG. 6A, without repeating a process of generating the similar patterns and calculating the support for each interest pattern model, the set of similar that fulfill a condition of the maximum allowed mismatch value is obtained, and the support of the similar patterns are calculated. After these operations, whether the candidate pattern fulfills the conditions of the plurality of interest pattern models may be determined using the supports and mismatch values of the similar patterns that have already been obtained.

FIG. 6B is a diagram illustrating an example of determining whether a child candidate pattern 'aaa' of a candidate pattern 'aa' fulfills the conditions of an interest pattern model. In the example of FIG. 6B, a similar pattern 'bbb' among similar patterns of the child candidate pattern 'aaa' has a mismatch value 3, which is greater than the greatest allowed mismatch value 2 of P1 and P2. Thus, the similar pattern 'bbb' is not included in a set of similar patterns. Also, a support sum of the similar patterns 'aaa', 'aab', 'aba', 'abb', 'baa', 'bab', and 'bba' that fulfill a condition of an allowed mismatch value 2 of P2 is 7, so the child pattern 'aaa' fulfills the condition of a minimum support 5 of P2. However, a support sum of the similar patterns 'aaa', 'aab', 'aba', and 'baa' that fulfill a condition of the allowed mismatch value 1 of P1 is 4, so the child pattern 'aaa' does not fulfill the condition of a minimum support 5 of P1.

Figure 7:
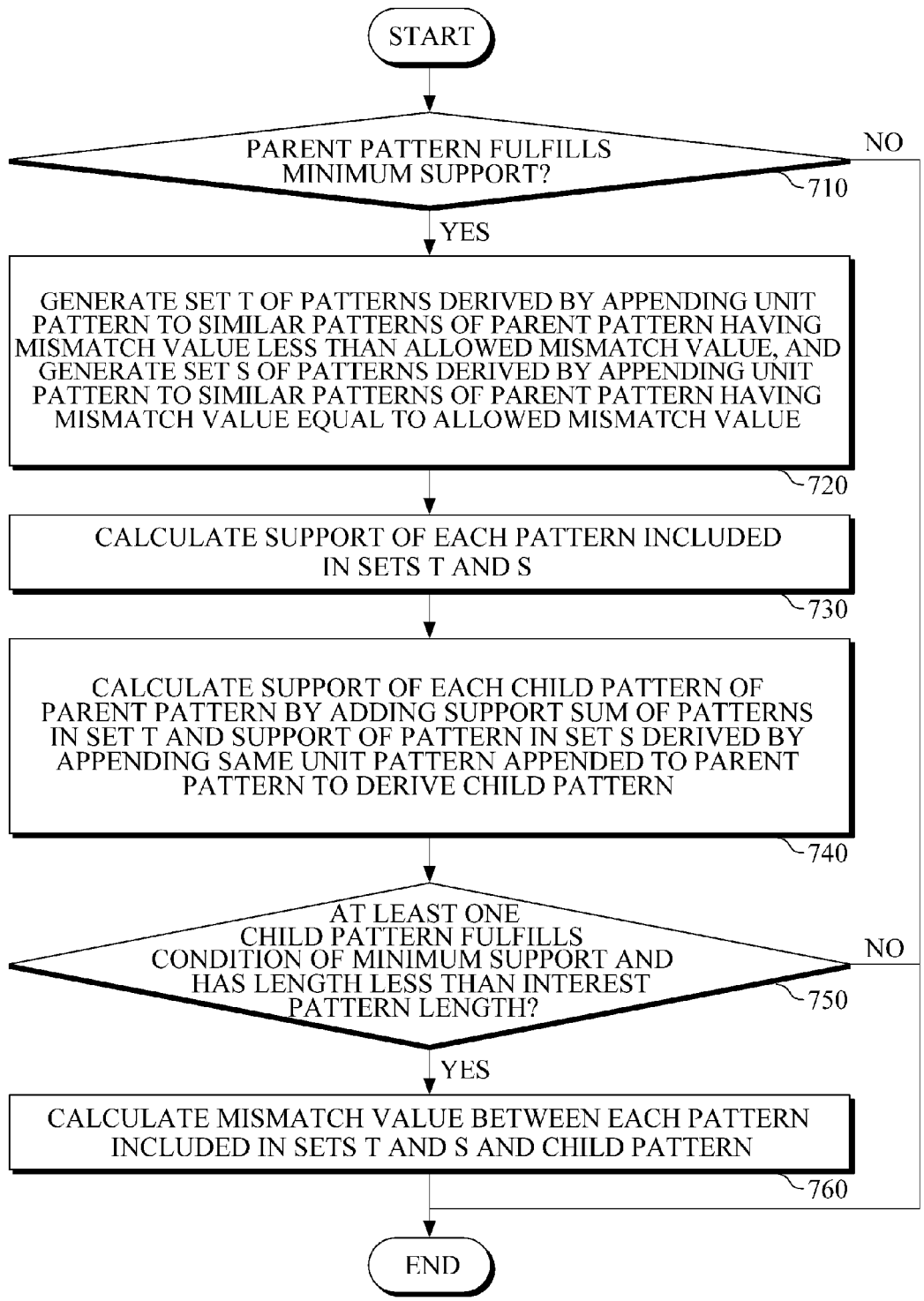
FIG. 7 is a flowchart illustrating an example of a method of searching a pattern using a mismatch value of a parent pattern.
Figure 8:
FIG. 8 is a diagram illustrating an example of a method of searching a pattern using a mismatch value of a parent pattern.

FIG. 7 is a flowchart illustrating an example of a method of searching a pattern using a mismatch value of a parent pattern. FIG. 8 is a diagram illustrating an example of a method of searching a pattern using a mismatch value of a parent pattern.

In the example of FIG. 8, an interest pattern model is P=(L: 3-4, D: 2, K: 6), and 'a' and 'b' are available unit patterns.

Referring to FIGS. 7 and 8, in a case of a parent pattern 'aa', a support sum of similar patterns that fulfill a condition of an allowed mismatch value of P is 7, which accordingly fulfills a condition of a minimum support 6 of P. In a case where a parent pattern fulfills a minimum support of an interest pattern model in 710, sets S and T of patterns are generated in 720, wherein the set S is derived by appending a unit pattern to the parent pattern's similar patterns whose mismatch values are equal to the allowed mismatch value, and the set T is derived by appending a unit pattern to the parent pattern's similar patterns whose mismatch values are less than the allowed mismatch value.

More specifically, the child pattern is a pattern generated by appending a unit pattern to the parent pattern. Thus, although any unit pattern is appended to similar patterns of the parent pattern, a mismatch value may increase 1 at most compared to the child pattern. Accordingly, even though any unit pattern is appended to the similar patterns of the parent pattern, if each similar pattern has a mismatch value less than an allowed mismatch value of the interest pattern model, the mismatch value of the similar pattern of the child pattern compared to the child pattern will not be greater than the allowed mismatch value of the interest pattern model.

Also, in a case of the parent pattern's similar patterns whose mismatch value compared to the parent pattern is equal to the allowed mismatch value of the interest pattern model, even though a unit pattern the same as the unit pattern appended to the parent patent to derive the child pattern is appended to the similar patterns of the parent pattern, the mismatch values of the similar patterns of the child pattern compared to the child pattern will not be greater than the allowed mismatch value of the interest pattern model.

Conversely, in a case of the parent pattern's similar patterns whose mismatch values compared to the parent pattern are equal to the allowed mismatch value of the interest pattern model, if a unit pattern different from a unit pattern appended to the parent pattern to derive the child pattern is appended to the similar patterns of the parent pattern, the mismatch values of the similar patterns of the child pattern compared to the child pattern will be greater than the allowed mismatch value of the interest pattern model.

In a case of the parent pattern's similar patterns whose mismatch values compared to the parent pattern are greater than the allowed mismatch value of the interest pattern model, the mismatch values of the similar patterns of the child pattern compared to the child pattern will be greater than the allowed mismatch value of the interest pattern model no matter which unit pattern is appended to the similar patterns of the parent pattern.

In other words, referring to FIG. 8, a set T of patterns 'aaa', 'aab', 'aba', 'abb', 'baa', 'bab' (namely, T={aaa, aab, aba, abb, baa, bab}) is derived by appending the unit patterns 'a' and 'b' to similar patterns 'aa', 'ab', and 'ba' of a parent pattern 'aa' whose mismatch values are less than the allowed mismatch value 2 of the interest pattern model P. The patterns included in the set T are included in a set of similar patterns of each of child patterns 'aaa' and 'aab', and have mismatch values that are not greater than the allowed mismatch value 2 of the interest pattern model P compared to each of the child patterns 'aaa' and 'aab'.

Also, a set S of patterns 'bba' and 'bbb' (namely, S={bba, bbb}) is derived by appending the unit patterns 'a' and 'b' to a similar pattern 'bb' of the parent pattern 'aa' that has the mismatch value 2 equal to the allowed mismatch value 2 of P. The patterns included in the set S are included in the set of similar patterns of each of the child patterns 'aaa' and 'aab'. The mismatch values of the patterns included in the set S are not greater than the allowed mismatch value 2 compared to the child pattern for those patterns included in the set S that are derived by appending a unit pattern to the similar pattern that is the same as a unit pattern appended to the parent pattern to derive the child pattern. On the other hand, the mismatch values of the patterns included in the set S are greater than the allowed mismatch value compared to the child pattern for those patterns included in the set S that are derived by appending a unit pattern to the similar pattern that is different from a unit pattern appended to the parent pattern to derive the child pattern.

In other words, in FIG. 8, the mismatch value 2 of 'bba' included in the set S compared to the child pattern 'aaa' is not greater than the allowed mismatch value 2. However, the mismatch value 3 of 'bbb' included in the set S compared to the child pattern 'aaa' is greater than the allowed mismatch value 2. In addition, the mismatch value 2 of 'bbb' included in the set S compared to the child pattern 'aab' is not greater than the allowed mismatch value 2. However, the mismatch value 3 of 'bba' included in the set S compared to the child pattern 'aab' is greater than the allowed mismatch value 2.

Thus, whether the child patterns fulfill the conditions of the interest pattern model may be determined using a support of each pattern included in the sets T and S.

Referring to FIG. 7 again, after the sets T and S are generated in 720, the support of each of the patterns included in the sets T and S are calculated in 730. Afterwards, using the supports of the patterns included in the sets T and S, the supports of child patterns generable from the parent pattern 'aa' are calculated in 740.

More specifically, in FIG. 8, a support of a child pattern 'aaa' is equal to a sum of a support sum of all patterns included in the set T and a support of 'bba' among the patterns included in the set S. Thus, as illustrated in FIG. 8, the support of the child pattern 'aaa' is 6, which means that the child pattern 'aaa' fulfills the condition of the minimum support 6 of the interest pattern model P.

Moreover, a support of the child pattern 'aab' is equal to a sum of the support sum of all patterns included in the set T and a support of 'bbb' among the patterns included in the set S. Thus, the support of the child pattern 'aab' is 7, which means that the child pattern 'aab' fulfills the condition of the minimum support 6 of the interest pattern model P.

In other words, without repeating processes of generating a set of similar patterns for each child pattern and calculating supports of the similar patterns included in each set, supports of all child patterns may be calculated using only the supports of the patterns included in the sets T and S. As a result, processes for generating the similar patterns and calculating supports of the similar patterns may be decreased to save a lot of time.

In the example illustrated in FIGS. 7 and 8, the child patterns 'aaa' and 'aab' fulfill the minimum support condition 6 of the interest pattern model, and also the length 3 of 'aaa' and 'aab' is less than the maximum interest pattern length 4 in the interest pattern model in 750. As a result, whether grandchild that can be generated from each of the child patterns 'aaa' and 'aab' fulfill the minimum support condition of the interest pattern model may be determined. More specifically, after obtaining a mismatch value between each pattern included in the sets T and S and the child pattern 'aaa' in 760, whether supports of grandchild patterns 'aaaa' and 'aaab' that can be generated from 'aaa' are greater than the minimum support of the interest pattern model may be determined using such mismatch values. Also, after obtaining a mismatch value between each pattern included in the sets T and S and the child pattern 'aab' in 760, whether supports of grandchild patterns 'aaba' and 'aabb' that can be generated from 'aab' are greater than the minimum support of the interest pattern model may be determined using such mismatch values.

Meanwhile, unlike the example of FIG. 8, in a case where none of the child patterns fulfill the condition of the minimum support of the interest pattern model, the grandchild patterns also will not fulfill the minimum support condition of the interest pattern model. As a result, whether the grandchild patterns fulfill the minimum support condition need not be determined.

Also, even if a child pattern fulfills the minimum support condition of the interest pattern model, in a case where the length of the child pattern is equal to the maximum interest pattern length of the interest pattern model, the length of the grandchild pattern will be greater than the maximum interest pattern length of the interest pattern model, so whether the grandchild pattern fulfills the minimum support condition of the interest pattern model need not be determined.

Figure 9:
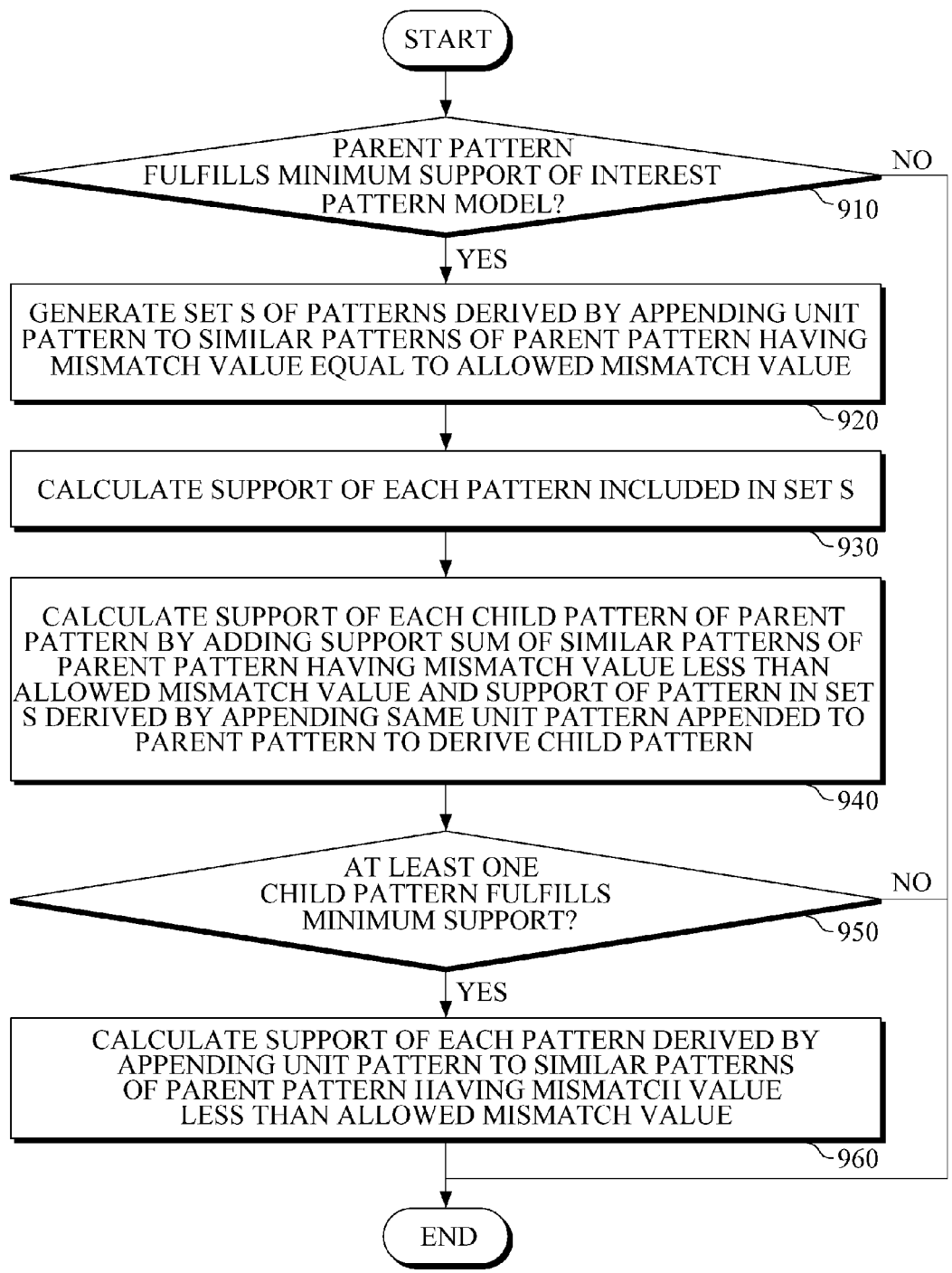
FIG. 9 is a flowchart illustrating an example of searching a pattern using a support of a parent pattern.

FIG. 9 is a flowchart illustrating an example of searching a pattern using a support of a parent pattern.

Referring to FIGS. 8 and 9, a support sum of similar patterns of parent pattern 'aa' that fulfill a condition of an allowed mismatch value 2 of the interest pattern model P is 7. As a result, the parent pattern 'aa' fulfills a condition of a minimum support of P. In a case where the parent pattern fulfills the condition of the minimum support of the interest pattern model in 910, a set S of patterns is generated in 920, and the support of each of the patterns included in the set S is calculated in 930, wherein the patterns in the set S are derived by appending a unit pattern to similar patterns of the parent pattern whose mismatch values 2 are equal to the allowed mismatch value 2. In one example, the support of the patterns included in the set S may be calculated using a data structure for searching a support that is generated and stored in advance.

In one example, all patterns included in the set T and S as illustrated in FIG. 8 are included in a set of all similar patterns of child patterns 'aaa' and 'aab'. By adding a support sum of patterns included in the set T and a support of a pattern in the set S derived by appending a same unit pattern that is appended to the parent pattern to derive the child pattern, supports of all of the child patterns can be calculated. In the example in FIG. 8, it may be determined that the support sum of the patterns included in the set T is equal to the support sum of similar patterns 'aa', 'ab', and 'ba' among similar patterns of the parent pattern whose mismatch value is less than the allowed mismatch value of the interest pattern model P.

Accordingly, in the example, a support of the child pattern may be calculated in 940 by adding a support sum of similar patterns of the parent pattern having a mismatch value less than an allowed mismatch value of the interest pattern model and the support of a pattern in the set S derived by appending a same unit pattern that is appended to the parent pattern to derive the child pattern. That is, without repeating, for each child pattern, both generating a set of similar patterns and calculating supports of similar patterns included in the set of similar patterns, supports of all child patterns can be calculated using the support of patterns in the set S. As a result, processes for generating similar patterns and calculating their supports, which are relatively time consuming, may be reduced.

More specifically, as illustrated in FIG. 8, a support of the child pattern 'aaa' is equal to a value calculated by adding the support of 'bba' included in the set S and a support sum of 'aa', 'ab', and 'ba' included in the similar patterns of the parent pattern 'aa'. Accordingly, the support of the child pattern 'aaa' is 6, which fulfills the minimum support condition 6 of the interest pattern model P.

Also, a support of the child pattern 'aab' is equal to a value calculated by adding the support of 'bbb' included in the set S and a support sum of 'aa', 'ab', and 'ba' included in the similar patterns of the parent pattern 'aa'. Accordingly, the support of the child pattern 'aab' is 7, which fulfills the minimum support condition 6 of the interest pattern model P.

In one example, if at least one child pattern fulfills a condition of a minimum support of an interest pattern model in 950, a process of calculating a support of patterns derived by appending a unit pattern to similar patterns whose mismatch value is less than an allowed mismatch value among similar patterns of a parent pattern may be used to calculate supports of grandchild patterns that have the child patterns as parent patterns in 960. However, if none of the child patterns fulfills a condition of the minimum support condition of the interest pattern model in 950, whether the grandchild patterns fulfill the conditions of the interest pattern model need not be determined.

In another example, even if at least one child pattern fulfills a condition of a minimum support of the interest pattern model, if a length of the child pattern is equal to an interest pattern length of the interest pattern model, a length of a grandchild pattern will be greater than the interest pattern length, so whether the grandchild pattern fulfills the conditions of the interest pattern model need not be determined.

Figure 10:
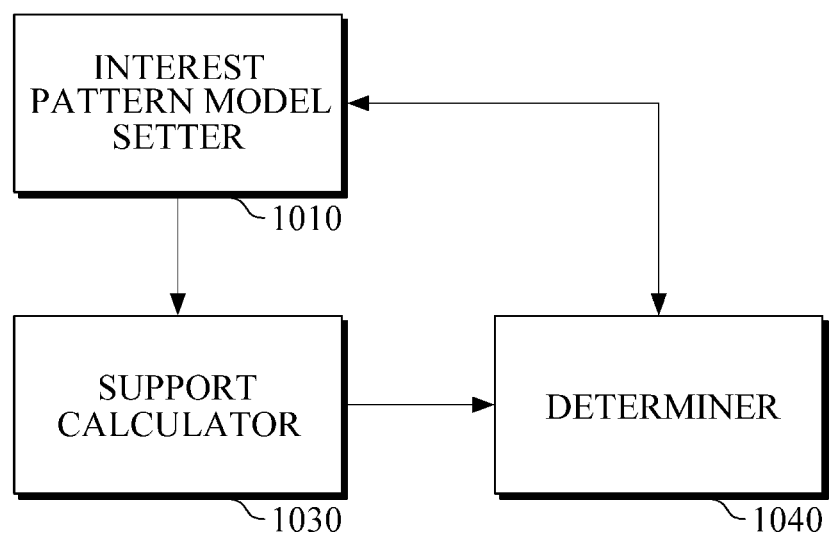
FIG. 10 is a diagram illustrating an example of an apparatus for searching a pattern in sequence data.

FIG. 10 is a diagram illustrating an example of an apparatus for searching a pattern in sequence data. Referring to FIG. 10, the apparatus for searching a pattern in sequence data includes an interest pattern model setter 1010, a support calculator 1030, and a determiner 1040.

An interest pattern model setter 1010 sets a plurality of interest pattern models each including an interest pattern length, an allowed mismatch value, and a minimum support. The interest pattern models may be set by a user. In one example, if an exact form of meaningful patterns in sequence data is known, the user can set the interest pattern model by setting an interest pattern length, an allowed mismatch value, and a minimum support.

In another example, if a rough form of meaningful patterns in sequence data is known, the user can set a plurality of interest pattern models each having any one or any combination of a different interest pattern length, a different allowed mismatch value, and a different minimum support. For example, the plurality of interest pattern models may have the same interest pattern length and the same allowed mismatch value, but different minimum supports. Or, for example, the plurality of interest pattern models may have the same interest pattern length and the same minimum support, but different allowed mismatch values. Or, for example, the plurality of interest pattern models may have the same allowed mismatch value and the same minimum support, but different interest pattern lengths. Or, for example, the plurality of interest pattern models may have different interest pattern lengths, different allowed mismatch values, and different minimum supports. As will be understood by one of ordinary skill in the art, many other combinations are also possible.

A support calculator 1030 calculates a support of each candidate pattern that is generable within the interest pattern length based on the allowed mismatch value of the interest pattern model. Also, the determiner 1040 determines whether the candidate pattern fulfills a condition of the minimum support of a plurality of interest pattern models using the support of the candidate patterns calculated by the support calculator 1030.

In one example, if the allowed mismatch values of the plurality of interest pattern models are the same, the support calculator 1030 generates a set of similar patterns that include similar patterns whose mismatch value compared to the candidate pattern is less than the allowed mismatch value of the interest pattern model, and calculates the support of each similar pattern included in the set of similar patterns.

In one example, the determiner 1040 determines whether a support sum of the similar patterns included in the set is greater than or equal to a minimum support of each interest pattern model.

In one example, if the plurality of interest pattern models have different allowed mismatch values, the support calculator 1030 generates a set of similar patterns that include similar patterns whose mismatch value compared to the candidate pattern is within a range of a maximum allowed mismatch value of the plurality of interest pattern models, and calculates the support of each similar pattern included in the set of similar patterns.

In one example, the determiner 1040 determines whether a support sum of similar patterns that fulfill a condition of the allowed mismatch value in the set fulfills a condition of the minimum support for each of the plurality of interest pattern models.

For example, if the allowed mismatch values of two interest pattern models are set to 2 and 3, the support calculator 1030 generates a set of similar patterns that include similar patterns whose allowed mismatch value compared to a candidate pattern is within a range of the maximum allowed mismatch value 3, and calculates a support of each similar pattern included in the set.

If the allowed mismatch value of the interest pattern model is 3, a support sum of all similar patterns whose mismatch value compared to the candidate pattern is less than or equal to 3 is equal to the support of the candidate pattern. Also, if the allowed mismatch value of the interest pattern model is 2, a support sum of similar patterns included in the set whose mismatch value compared to the candidate pattern is less than or equal to 2 is equal to the support of the candidate pattern.

Accordingly, the determiner 1040 may determine whether the support sum of all similar patterns included in the set is greater than the minimum support of the interest pattern model that includes the allowed mismatch value 3. In addition, the determiner 1040 may determine whether the support sum of similar patterns included in the set whose mismatch value is less than or equal to 2 is greater than a minimum support of the interest pattern model that includes the allowed mismatch value 2.

In one example, a support for each similar pattern may be calculated using a data structure for searching a support that has already been acquired from sequence data in advance. In a case where the sequence data is input, the data structure for searching a support may be generated in advance and stored in a memory or on a disk.

In one example, the data structure for searching the support may use a suffix tree. For example, if the sequence data is composed of a combination of unit patterns 'a' and 'b', the suffix tree may provide information about the support of all available patterns starting with the unit pattern 'a' or 'b'.

That is, if the suffix tree for searching the support in the sequence data has already been generated in advance and stored, a support of a specific pattern can be quickly calculated using path information in the suffix tree.

However, the data structure for searching the support is not limited to the suffix tree. Various other types of data structures may be used, such as a hash table or any other type of data structure known to one of ordinary skill in the art.

In one example, if a support of a candidate pattern fulfills a condition of at least one minimum support of a plurality of interest pattern models, and the candidate pattern length is less than a maximum interest pattern length of at least one interest pattern model that the candidate pattern fulfills, the support calculator 1030 may calculate supports of child patterns that can be derived from the candidate pattern using a mismatch value derived after comparing the similar pattern to the candidate pattern. Also, the determiner 1040 may determine whether the child pattern fulfills the conditions of the interest pattern model that the candidate pattern fulfills.

The interest pattern model setter 1010, the support calculator 1030, and the determiner 1040 in FIG. 10 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of searching a pattern in sequence data, the method comprising:
    setting a plurality of interest pattern models each comprising an interest pattern length, an allowed mismatch value, and a minimum support;
    determining a candidate pattern that is within an interest pattern length of at least one of the plurality of interest pattern models;
    controlling a processor to access a predetermined structure of the sequence data in a memory and calculate a support for the candidate pattern in the sequence data based on an allowed mismatch value of the at least one of the plurality of interest pattern models; and
    determining whether the support fulfills a condition of the minimum support of the at least one of the plurality of interest pattern models,
    wherein the determining of whether the support fulfills the condition of the minimum support of the at least one of the plurality of interest pattern models comprises determining, for each of the plurality of interest pattern models, whether a support sum of similar patterns in a set fulfilling a condition of the allowed mismatch value of the interest pattern model fulfills the condition of the minimum support of the interest pattern model.

2. The method of claim 1, wherein the controlling of the processor further comprises calculating a support for a candidate pattern that is within a maximum interest pattern length of the plurality of the interest pattern models.

3. The method of claim 1, wherein the controlling of the processor further comprises, in response to the allowed mismatch value being the same in each of the plurality of interest pattern models:
    generating a set of similar patterns having a mismatch value compared to the candidate pattern within a range of the allowed mismatch value; and
    calculating a support of each of the similar patterns in the set.

4. The method of claim 3, wherein the determining of whether the support for the candidate pattern fulfills the condition of the minimum support of at least one of the plurality of interest patter models comprises determining whether a support sum of the similar patterns in the set fulfills a condition of the minimum support of each of the plurality of interest pattern models.

5. The method of claim 1, wherein the controlling of the processor further comprises, in response to the allowed mismatch value being different in at least two of the plurality of interest pattern models:
    generating a set of similar patterns having a mismatch value compared to the candidate pattern within a range of a maximum allowed mismatch value of the plurality of interest pattern models; and
    calculating a support of each of the similar patterns in the set.

6. The method of claim 1, wherein the calculating of the support for the candidate pattern includes calculating a sum of supports of determined similar patterns for the candidate pattern.

7. The method of claim 1, wherein the controlling of the processor to access the predetermined structure of the sequence data further comprises controlling an accessing of the predetermined structure by one or more processing devices, and the calculating of the support of the candidate pattern further comprises calculating, by at least one of the one or more processing devices, a sum of respectively determined supports, of determined similar patterns of the candidate pattern, which are based on the accessed predetermined structure,
    wherein the determining of whether the support for the candidate pattern fulfills the condition further comprises determining whether the candidate pattern fulfills conditions of at least two of the plurality of interest pattern models, which have different allowed mismatch values, based on the sum.

8. The method of claim 1, wherein a calculated support for a pattern in the sequence data indicates a number of times the pattern appears in the sequence.

9. A method of searching a pattern in sequence data, the method comprising:
setting a plurality of interest pattern models each comprising an interest pattern length, an allowed mismatch value, and a minimum support;
controlling a processor to calculate a support of a parent pattern in the sequence data through an accessing of a predetermined structure of the sequence data in a memory; and
in response to determining whether the support of the parent pattern is greater than or equal to the minimum support, calculating a support of a child pattern, of the parent pattern, based on the allowed mismatch value of the at least one interest pattern model and determining whether the support of the child pattern fulfills a condition of the minimum support of the at least one interest pattern model,
wherein the determining of whether the support of the child pattern fulfills the condition of the minimum support of the at least one interest pattern model comprises determining, for each of the at least one interest pattern model, whether a support sum of similar patterns in a set fulfilling a condition of the allowed mismatch value of the interest pattern model fulfills a condition of the minimum support of the interest pattern model.

10. The method of claim 9, wherein the calculating of the support of the child pattern comprises calculating the support of the child pattern in response to a parent pattern length of the parent pattern being less than a maximum interest pattern length of the at least one interest pattern model.

11. The method of claim 9, wherein the calculating of the support of the child pattern comprises, in response to the allowed mismatch value being the same in each of the at least one interest pattern model, calculating the support of the child pattern by:
generating a set of similar patterns within a range of the allowed mismatch value of the at least one interest pattern model; and
calculating a support of each of the similar patterns in the set.

12. The method of claim 11, wherein the determining of whether the support of the child pattern fulfills the condition of the minimum support of the at least one interest pattern model comprises determining whether a support sum of the similar patterns in the set fulfills a condition of the minimum support of each of the at least one interest pattern model.

13. The method of claim 9, wherein the calculating of the support of the child pattern comprises:
generating a set of similar patterns within a range of a maximum allowed mismatch value of the at least one interest pattern model; and
calculating a support of each of the similar patterns in the set.

14. A method of searching a pattern in sequence data, the method comprising:
setting an interest pattern model comprising an interest pattern length, an allowed mismatch value, and a minimum support;
controlling a processor to calculate a support of a parent pattern, including accessing a predetermined structure of the sequence data in a memory; and
in response to determining whether the support of the parent application is greater than or equal to the minimum support, calculating a support of a child pattern of the parent pattern using mismatch values of similar patterns of the parent pattern,
wherein the calculating of the support of the child pattern comprises:
generating a first set of patterns by appending a unit pattern to similar patterns of the parent pattern having a mismatch value less than the allowed mismatch value;
generating a second set of patterns by appending a unit pattern to similar patterns of the parent pattern having a mismatch value equal to the allowed mismatch value;
calculating a support of each of the patterns in the first set and the second set; and
calculating the support of the child pattern using the support of each of the patterns in the first set and the second set.

15. The method of claim 14, wherein the calculating of the support of the child pattern further comprises:
generating the child pattern by appending a unit pattern to the parent pattern;
adding a sum support of the patterns in the first set and a support of a pattern in the second set derived by appending a same unit pattern appended to the parent pattern to generate the child pattern; and
determining whether a result of the adding fulfills a condition of the minimum support.

16. The method of claim 14, further comprising, in response to at least one child pattern derived from the parent pattern fulfilling a condition of the minimum support and having a length less than the interest pattern length, calculating a mismatch value by comparing each of the at least one child fulfilling the condition of the minimum support with each of the patterns in the first set and the second set.

17. A method of searching a pattern in sequence data, the method comprising:
setting an interest pattern model comprising an interest pattern length, an allowed mismatch value, and a minimum support;
controlling a processor to calculate a support of a parent pattern, including accessing a predetermined structure of the sequence data in a memory;
in response to determining whether the support of the parent pattern is greater than or equal to the minimum support, calculating a support of a child pattern of the parent pattern using mismatch values and supports of similar patterns of the parent pattern; and
determining of whether the support of the child pattern fulfills the condition of the one minimum support of the at least one interest pattern model comprises determining, for each of the at least one interest pattern model, whether a support sum of similar patterns in the set fulfilling a condition of the allowed mismatch value of the interest pattern model fulfills a condition of the minimum support of the interest pattern model.

18. The method of claim 17, wherein the calculating of the support of the child pattern comprises:
generating a set of patterns by appending a unit pattern to similar patterns of the parent pattern having a mismatch value equal to the allowed mismatch value;
calculating a support of each of the patterns in the set; and
calculating the support of the child pattern using the support of the patterns in the set and a support of similar patterns of the parent pattern having a mismatch value less than the allowed mismatch value.

19. The method of claim 18, wherein the calculating of the support of the child pattern further comprises:

generating the child pattern by appending a unit pattern to the parent pattern; and calculating the support of the child pattern by adding the support of each of the patterns in the set derived by appending a same unit pattern appended to the parent pattern to generate the child pattern, and the support of each of the similar patterns having the mismatch value less than the allowed mismatch value.

20. The method of claim 17, further comprising, in response to at least one child pattern of the parent pattern fulfilling a condition of the minimum support and having a length less than the interest pattern length:

generating a set of patterns by appending a unit pattern to similar patterns of the parent pattern having a mismatch value less than the allowed mismatch value; and calculating a support of each of the patterns in the set.

21. An apparatus for searching a pattern in sequence data, the apparatus comprising:

an interest pattern model setter configured to set a plurality of interest pattern models each comprising an interest pattern length, an allowed mismatch value, and a minimum support;

a support calculator comprising a processor configured to calculate a support for a candidate pattern which is within the interest pattern length of at least one of the plurality of interest pattern models, for the sequence data, through an accessing of a predetermined structure of the sequence data in a memory and based on the allowed mismatch value of at least one of the plurality of interest pattern models; and a determiner configured to determine whether the support fulfills a condition of the minimum support of at least one of the plurality of interest pattern models, wherein, in response to the support of the candidate pattern fulfilling the condition of the minimum support of the at least one of the plurality of interest pattern models and the candidate pattern having a length less than a maximum interest pattern length of the at least one of the plurality of interest pattern models, the support calculator is further configured to calculate a support of a child pattern that is generable from the candidate pattern using a mismatch value of each pattern of similar patterns of the candidate pattern; and the determiner is further configured to determine whether the child pattern fulfills conditions of the at least one of the plurality of interest pattern models of which the condition of the minimum support is fulfilled by the candidate pattern.

22. The apparatus of claim 21, wherein, in response to the allowed mismatch value being the same in each of the plurality of interest pattern models, the support calculator is further configured to:

generate a set of similar patterns having a mismatch value compared to the candidate pattern within a range of the allowed mismatch value; and calculate a support of each of the similar patterns in the set.

23. The apparatus of claim 22, wherein the determiner is further configured to determine whether a support sum of the similar patterns in the set fulfills a condition of the minimum support of each of the plurality of interest pattern models.

24. The apparatus of claim 21, wherein, in response to the allowed mismatch value being different in at least two of the plurality of interest pattern models, the support calculator is further configured to:

generate a set of similar patterns having a mismatch value compared to the candidate pattern within a range of a maximum allowed mismatch value of the plurality of interest pattern models; and calculate a support of each of the similar patterns in the set.

25. The apparatus of claim 24, wherein the determiner is further configured to determine, for each of the plurality of interest pattern models, whether a support sum of similar patterns in the set fulfilling a condition of the allowed mismatch value of the interest pattern model fulfills the condition of the minimum support of the interest pattern model.

26. A method of searching a pattern in sequence data, the method comprising:

setting a plurality of interest pattern models each comprising an interest pattern length, an allowed mismatch value, and a minimum support, wherein the allowed mismatch value is different in each of the plurality of interest pattern models;

generating all possible similar patterns of a candidate pattern within the interest pattern length;

controlling a processor to access a predetermined structure of the sequence data in a memory and calculate a support and a mismatch value of each of the similar patterns with respect to the sequence data; and determining, for each of the plurality of interest pattern models, whether the candidate pattern fulfills conditions of the interest pattern model based on the support of only those similar patterns having a mismatch value less than or equal to the mismatch value of the interest pattern model, wherein the determining comprises:

calculating a support sum of only those similar patterns having a mismatch value less than or equal to the mismatch value of the interest pattern model;

comparing the support sum with the minimum support of the interest pattern model;

in response to the support sum being greater than or equal to the minimum support of the interest pattern model, determining that the candidate pattern fulfills the conditions of the interest pattern model; and in response to the support sum being less than the minimum support of the interest pattern model, determining that the candidate pattern does not fulfill the conditions of the interest pattern model.

27. The method of claim 26, wherein the minimum support is different in each of the plurality of interest pattern models.

28. A method of searching a pattern in sequence data, the method comprising:

setting a plurality of interest pattern models each comprising an interest pattern length, an allowed mismatch value, and a minimum support;

determining a candidate pattern, which is within an interest pattern length of at least one of the plurality of interest pattern models, and determining similar patterns of the candidate pattern;

controlling a processor to access a predetermined structure of the sequence data, respectively calculating support of each of the similar patterns in the sequence data, based on a minimum allowed mismatch value of the plurality of interest pattern models, and to calculate a sum of the respectively calculated supports of the similar patterns; and determining whether the candidate pattern fulfills conditions of all of the plurality of interest pattern models based at least on the calculated sum, wherein the calculating of the sum of the respectively determined supports of the similar patterns comprises:

calculating the sum as a first sum of respectively determined supports of similar patterns corresponding to a first interest pattern model having the minimum allowed mismatch value of the mismatch values of the plurality of interest pattern models; and calculating a second sum of the first sum and respectively determined supports of similar patterns of the candidate pattern corresponding to a mismatch value, greater than the minimum mismatch value, of a second interest pattern model of the plurality of interest pattern models.

29. The method of claim 28, wherein the determining of whether the candidate pattern fulfills the conditions of all of the plurality of interest pattern models includes determining whether the first sum meets a minimum support of the first interest pattern model and whether the second sum meets a minimum support of the second interest pattern model.

* * * * *